(12) United States Patent
Denis et al.

(10) Patent No.: US 6,872,190 B1
(45) Date of Patent: Mar. 29, 2005

(54) SAFETY ASSEMBLY FOR A SYRINGE PRE-FILLED WITH LIQUID, IN PARTICULAR A MEDICINE

(75) Inventors: Roger Denis, Limoges (FR); Henriette Dorat, Limoges (FR)

(73) Assignee: Compagnie Plastic Omnium, Lyons (FR)

(*) Notice: Subject to any disclaimer, the term of this patent is extended or adjusted under 35 U.S.C. 154(b) by 0 days.

(21) Appl. No.: 09/857,144

(22) PCT Filed: Jun. 9, 1999

(86) PCT No.: PCT/FR99/01369

§ 371 (c)(1),
(2), (4) Date: Feb. 8, 2002

(87) PCT Pub. No.: WO00/33900

PCT Pub. Date: Jun. 15, 2000

(30) Foreign Application Priority Data

Dec. 8, 1998 (FR) .................................. 98 15628

(51) Int. Cl.⁷ .................................................. A61M 5/00
(52) U.S. Cl. ........................................ 604/110; 604/198
(58) Field of Search .............................. 604/48, 93.01, 604/181, 182, 186, 187, 188, 192, 193, 195, 196, 197, 198, 218, 110; 128/919

(56) References Cited

U.S. PATENT DOCUMENTS

| | | | |
|---|---|---|---|
| 4,932,947 A | 6/1990 | Cardwell | |
| 5,116,326 A | 5/1992 | Schmidt | |
| 5,492,536 A | 2/1996 | Mascia | |
| 5,562,626 A | 10/1996 | Sanpietro | |
| 2002/0004649 A1 * | 1/2002 | Jansen et al. | 604/198 |

FOREIGN PATENT DOCUMENTS

EP    0 405 039 A1    1/1991

* cited by examiner

Primary Examiner—LoAn T. Thanh
(74) Attorney, Agent, or Firm—Oliff & Berridge, PLC (57) ABSTRACT

The syringe (S) comprises a body (K) forming a liquid reservoir, carrying a needle (A) for injecting the liquid, and having a plunger (P) movably mounted in the body (K). The body (K) is housed in a safety sheath (1) to be axially movable between an active position in which the needle (A) projects through a distal end of the sheath (1) and a protection position in which the needle (A) is retracted inside the sheath (1) and towards which position the body (K) is urged resiliently. The body (K) is prevented from moving relative to the sheath in the active position by locking means (6) that opposite the resilient force on the body, and that are releasable by means (8) which are activated when the plunger (P) is in an end-of-liquid-injection position.

21 Claims, 6 Drawing Sheets

SAFETY ASSEMBLY FOR A SYRINGE PREFILLED WITH LIQUID, IN PARTICULAR A MEDICINE

BACKGROUND OF THE INVENTION

The present invention relates to a safety assembly for a syringe prefilled with injection liquid, in particular a medicine.

In the state of the art, a safety assembly is already known for a prefilled liquid injection syringe comprising a tubular body that forms a reservoir for the liquid, and that carries a needle for injecting the liquid and a plunger that is mounted in the body to be movable between a ready position and an end-of-injection position.

Usually, the plunger of a syringe has a drive end outside the body of the syringe and an end inside the body of said syringe that carries a piston. The drive end of the plunger is also known as a thumb rest.

Certain medical substances such as vaccines, heparins and derivatives thereof, and other accurately-dosed medicines, cannot be stored in containers or syringes made of plastics material because of the rate at which moisture is taken up, which would run the risk of compromising the composition.

Aware of these imperatives, laboratories are constrained to use only containers made of glass which presents no porosity. Given infectious virus diseases for which there is at present no antidote, safety is currently sought for providing all health care personnel with protection against any risk of possible contamination during professional accidents due to injections. This protection must come close to the 100% rate that the profession is calling for.

The problem is thus to fit a safety mechanism to syringes that are preferably made of glass, in particular syringes having capacity in the range 0.1 milliliters (ml) to 2 ml, since any type of mechanism internal to such syringes is unsuitable.

In addition, the requirement for sterility excludes any internal handling of a syringe once it has been filled.

Various solutions have been presented to laboratories and set aside for various reasons: increase in volume, modification to filling assembly lines, complex operations required of the doctor or the personnel using those proposals, pseudo-protection that is more harmful than useful.

It should be observed that numerous inventors can be criticized for their misleading use of language such as "a syringe having an automatically withdrawable needle" which, very often, turns out to be no more than a syringe which locks automatically, or a syringe having elements that can be destroyed, or having a cap or sliding tube to hide the needle after use.

In practice, a nurse holds a syringe between the index and middle fingers and presses with the thumb against the thumb rest. As a result, while the syringe is being held, the needle can be retracted only into a hollow plunger or piston, since the body of the syringe remains stationary.

In other cases, a sheath that slides longitudinally on the outside of the syringe "covers" the needle and thus in fact amounts to "retracting" the needle by advancing the sheath either manually or automatically.

Numerous patents are based on that known configuration which has been rejected by the medical profession because of the risk of the needle being pulled out or the patient suffering an incision as a result of the shock of the sheath striking the patient under the force of a spring urging the sheath into the needle-retraction position.

SUMMARY OF THE INVENTION

An object of the invention is to remedy the above-described drawbacks while satisfying the following criteria: good compactness, suitable for fitting to the end of a manufacturing line prior to packaging, safe for operating with one hand, automatic, controlled independently of human will, protection very close to the desired 100%.

To this end, the invention provides a safety assembly of the above-specified type, characterized in that it comprises:

a tubular sheath in which the body of the syringe is designed to be housed in axially displaceable manner between an active position in which the needle projects through a distal end of the sheath and a protection position in which the needle is retracted inside the sheath;

resilient return means for urging the body towards its protection position; and locking means for preventing the body from moving relative to the sheath in the active position by opposing the resilient force of the return means, said locking means being releasable by means activated when the plunger is in its end-of-injection position.

According to other characteristics of this assembly:

the sheath carries external retention means for being held by the fingers of a user to inject the liquid by moving a drive end of the plunger axially towards the retention means;

the retention means of the sheath comprise two substantially diametrically opposite fins or lugs;

the retention means comprise a shoulder formed on the outside surface of the sheath;

the body of the syringe has a proximal end provided with a flange, and the locking means comprise a seat against which the flange bears, which seat is formed in a proximal end of the sheath, and also comprises retractable means for clamping the flange against the seat, said means being carried by said proximal end of the sheath;

the retractable clamping means comprise at least one retractable catch;

the means for resiliently urging the body of the syringe into the protection position comprise a thrust spring designed to bear both against the flange of the body of the syringe and also against an internal bearing shoulder formed in the sheath between the bearing shoulder for the flange and the distal end of the sheath;

the means for releasing the locking means comprise a cap mounted to slide axially on the proximal end of the sheath between a ready position and a position for retracting the clamping catch, the cap being designed to be secured to the plunger at least during a portion of the displacement stroke of the plunger from its ready position to its end-of-injection position;

the cap has means for securing it to the plunger;

the cap and the proximal end of the sheath comprise complementary means for limiting the stroke of the cap in opposition to the resilient force of the means for returning the body after the locking means have been released;

the complementary means for limiting the stroke of the cap comprise complementary annular shoulders forming abutments that are provided on the sheath and the cap;

the complementary means for limiting the stroke of the cap comprise complementary snap-fastening means carried by the cap and the sheath;

the sheath and the cap are generally in the form of bodies of revolution and have complementary means for preventing relative rotation between each other;

the complementary means for preventing relative rotation of the sheath and the cap comprise at least one longitudinal groove formed in the cap and co-operating with a corresponding finger secured to the sheath;

the complementary means for preventing relative rotation of the sheath and the cap comprise at least one axial slot formed in the cap and co-operating with a fin;

the retractable clamping means comprise two arms hinged to the proximal end of the sheath (1) about a common transverse axis so as to form tongues for clamping the flange of the body of the syringe, each arm having an end for clamping the flange against its bearing seat and an end for driving the arm;

the drive ends of the arms co-operate with the retention lugs in such a manner as to be displaced when the plunger reaches its end-of-injection position from a position of forced clamping of the flange to a position of forced release of said flange, the passage from the forced clamping position to the forced release position taking place by passing through a hard point; and the user presses the fingers during injection of the liquid both against the retention lugs and the arms; and the proximal end of the sheath is extended by two longitudinal tabs for co-operating by snap-fastening with the flange of the body of the syringe so as to limit the stroke of said body after the locking means have been released.

BRIEF DESCRIPTION OF THE DRAWINGS

The invention will be better understood on reading the following description given purely by way of example and made with reference to the accompanying drawings, in which.

DETAILED DESCRIPTION OF THE EXEMPLARY EMBODIMENTS

Figure 1:
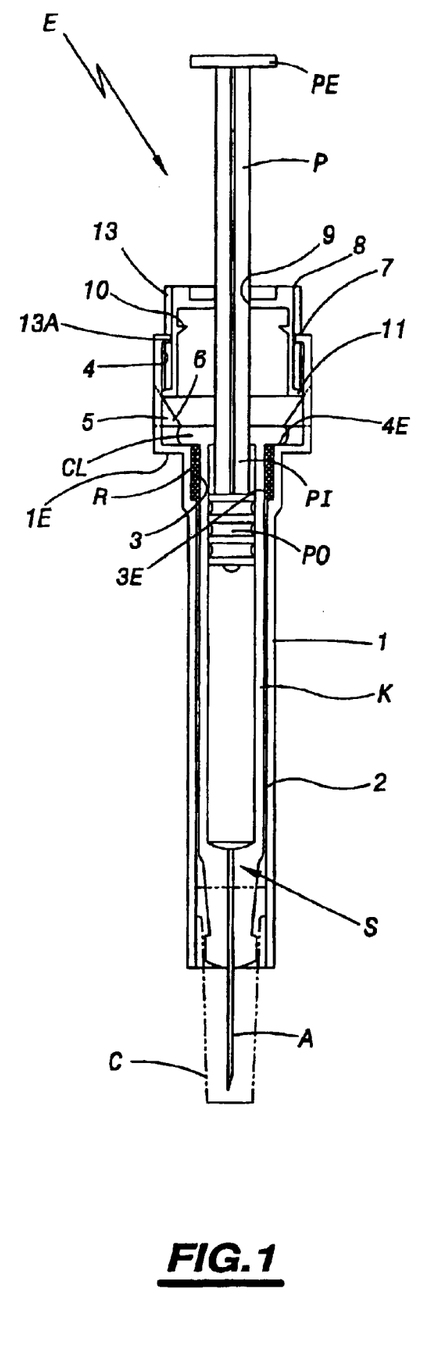
FIGS. 1 to 3 are axial section views of a safety assembly for a syringe and constituting a first embodiment of the invention and shown respectively in three configurations of use.
Figure 2:
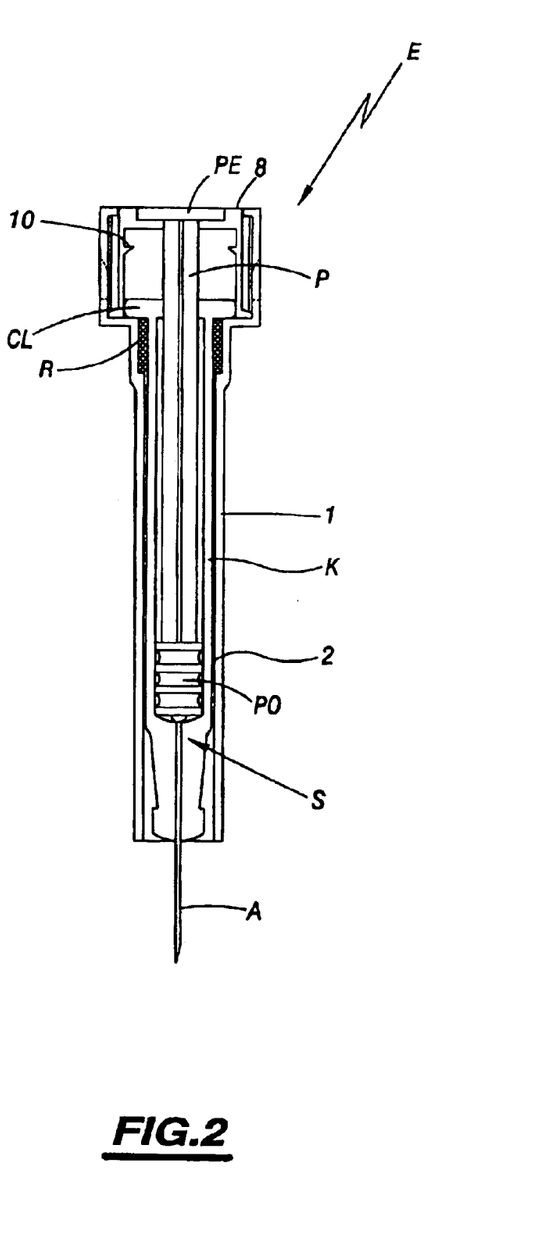
Figure 3:
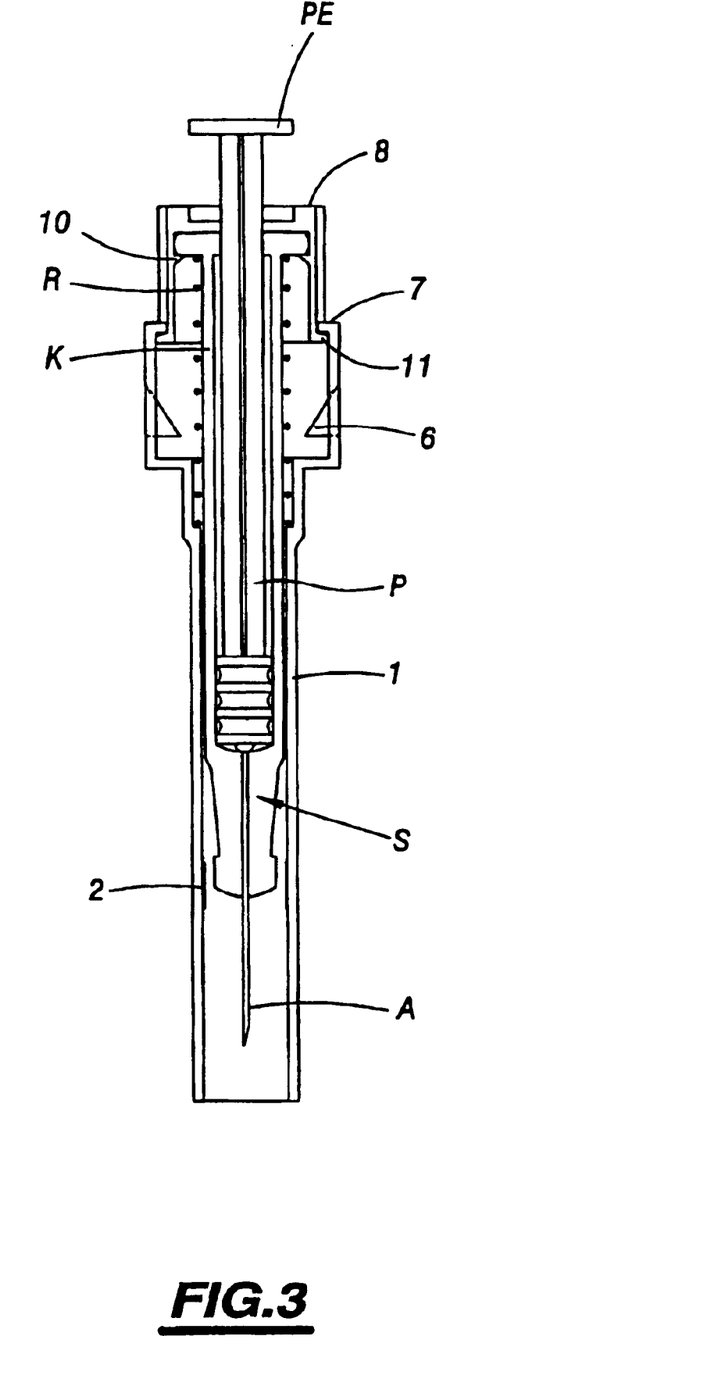

FIGS. 1 to 3 show a safety assembly for a conventional syringe S for injecting a liquid, in particular a medical liquid, and constituting a first embodiment of the invention. This safety assembly is given overall reference E.

The syringe S is prefilled, ready for use, and comprises a tubular body K forming a reservoir for the liquid, carrying a needle A for injecting the liquid, and having a plunger P mounted in the body K to slide between a ready position, as shown in FIG. 1, and an end-of-liquid-injection position as shown in FIG. 2.

The plunger P has a first end PE outside the body K and a second end PI inside the body K and carrying a conventional piston PO. The outside end PE forms an end for driving the plunger.

The assembly E comprises a tubular safety sheath in which the syringe is received, and in particular the body K. The sheath is a body of revolution and is constituted, for example, by a cylindrical tube 1 of plastics material or any other material that is sufficiently transparent to enable the liquid contained in the body K of the syringe to be seen together with any label for identifying the medicine. It will be observed that the cylindrical tube 1 is stepped.

In the description below, an element is referred to as "proximal" or "distal" depending on whether it is axially close to or remote from the outside end PE of the plunger.

The body K is held stationary relative to the tube 1 by locking means for preventing the syringe body from moving relative to the sheath or tube 1. The locking means comprise firstly a seat 4E against which the flange CL bears, the seat being formed by an internal shoulder defining the second housing 4, and secondly retractable means for clamping flange CL against the seat 4E and carried by the proximal end of the tube 1.

It will be observed that the body K of the syringe has a distal end carrying the needle A and a proximal end fitted with a flange CL.

The inside surface of the tube 1 has three guides 2 in relief extending in the longitudinal direction of the tube 1 and spaced apart from one another at 120° intervals, for the purpose of centering the body K of the syringe, reducing play, and improving the sliding of the body K inside the tube 1, while serving to pass a conventional rubber cover C (shown in chain-dotted lines in FIG. 1) that protects the needle A before the syringe is used.

The proximal end of the tube 1 carries, going upwards: a first cylindrical internal housing 3 extended by a second cylindrical internal housing 4 of diameter greater than that of the first internal housing.

The body K is held stationary relative to the tube 1 by locking means comprising firstly a seat 4E against which the flange CL bears, the seat being formed by an internal shoulder defining the second housing 4, and secondly retractable means for clamping the flange CL against the seat 4E and carried by the proximal end of the tube 1.

In the example shown in FIGS. 1 to 3, the retractable clamping means are formed by two tabs 5, that prevent the syringe body from moving relative to the sheath or tube 1, that are substantially diametrically opposite and that are partially cut out from the wall of the tube 1 where it defines the second housing 4. The tabs 5 are terminated by retractable catches 6 for holding the flange CL of the syringe body pressed against the seat 4E. It will be observed that the tabs 5 are folded so as to extend substantially in a diameter longitudinal plane of the tube. In a variant, the retractable clamping means could comprise a single tab 5 only.

The body K of the syringe is urged resiliently towards its protection position by a resilient return means, such as a thrust spring R placed in the first housing 3. This spring R bears firstly against an internal shoulder 3E defaming the first internal housing 3, and secondly against the flange CL of the body K of the syringe. The internal bearing shoulder 3E is disposed between the bearing seat 4E for the flange CL and the distal end of the tube 1.

In FIG. 1 which shows the safety assembly and the syringe ready for use, with the spring R compressed. The spring remains in this state until the liquid has finished being injected.

The catches 6 thus serve to prevent the body K moving relative to the tube 1 in the active position by opposing the resilient return force of the spring R.

It should be observed that the proximal end of the second internal housing 4 is defined by an internal ring 7 integrally molded with the tube 1.

The means for locking the body K of the syringe relative to the tube 1 can be released by means that are activated when the plunger P is in its end-of-injection position.

In the example shown in FIGS. 1 to 3, the means (release means) for releasing the locking means comprise a cylindrical cap 8, preferably made of plastics material, mounted to slide axially in the second housing 4 of the tube 1 between a high, ready position as shown in FIG. 1 and a position for retracting the catches 6, as shown in FIG. 2. The plunger P passes through the cap 8 and extends via a hole 9 formed in the proximal end of the cap 8.

The cap 8 also has snap-fastening means comprising internal catches 10 that are spaced apart by 90°, and also has an external ring 11 that is integrally molded with the distal end of the cap.

The internal ring 7 of the second housing 4 and the external ring 11 of the cap 8 define complementary annular shoulders forming abutments that limit the stroke of the cap 8 after the means for locking the body K have been released, opposing the resilient return force of the spring R (see FIG. 3). The complementary rings 7 and 11 thus act as a return limiter for the cap 8.

Depending on the type of syringe in particular, it is preferable for the tube 1 and the cap 8 to have complementary means for preventing relative rotation between them. By way of example, these complementary means for preventing rotation between the sheath or tube 1 and the cap 8 can comprise at least one longitudinal groove 13 formed in the cap 8 receiving a corresponding finger 13A that radially extends the internal ring 7 of the second housing 4. The cap preferably has two diametrically opposite grooves 13 as shown in FIGS. 1 to 3.

The syringe can be installed in the safety assembly E as follows.

Initially, the body K of the syringe is filled with the liquid that is to be injected. This liquid is retained in the body K by the piston PO. The plunger P is separate from the piston.

The body K of the prefilled syringe is placed in the tube 1 by snapping the flange CL beneath the catches 6 after compressing the spring R in the first housing 3.

Thereafter, the cap 8 is engaged in the second housing 4, e.g. being pressed into said second housing 4 until the external ring 11 comes into contact with the catches 6, as shown in FIG. 1.

Finally, the plunger P of the syringe is connected to the piston PO by inserting the distal end of the plunger into the cap 8 and the tube 1 through the orifice 9 of the cap 8.

The safety assembly E is then ready for use in the configuration shown in FIG. 1, with the needle A of the syringe projecting through the distal end of the tube 1.

In order to obtain an automatically-withdrawable needle and syringe effect, it is essential for the safety assembly E to be taken hold of via the protection tube 1 so as to enable the syringe fitted with its needle to withdraw freely and properly in line as soon as injection has terminated, i.e. without any risk for the patient. This provides an assembly E that is properly referred to as being of the type having an automatically-withdrawable needle.

The tube 1 is taken hold of by external retention means carried by the tube 1, for being held by the fingers of a user in order to inject the liquid by moving the external end PE of the plunger axially towards the retention means.

In the example shown in FIGS. 1 to 3, the external retention means of the tube 1 comprise a shoulder 1E formed in the outside surface of the tube 1.

In order to inject the liquid, the user takes hold of the assembly E between the index and middle fingers. The thumb exerts syringe pressure on the outside end PE of the plunger. The index and middle fingers retain the tube 1 by engaging the retention shoulder 1E.

The user pushes the plunger PE into the body of the syringe so as to bring the end PE of the plunger axially closer to the retention shoulder 1E, and this continues until the end-of-injection position as shown in FIG. 2 is reached.

The displacement stroke of the plunger P from its ready position to its end-of-injection position includes a final stroke during which the plunger P is engaged with the cap 8, preceded by an initial dead stroke of the plunger P relative to the cap 8 during which the cap 8 remains stationary. During the engagement stroke of the plunger P with the cap 8, the outside end PE of the plunger forming an engagement head co-operates with a setback defining the edge of the orifice 9 of the cap.

Because the cap 8 is entrained by the plunger P, the external ring 11 of the cap co-operates with the catches 6 so as to cause them to retract, as shown in FIG. 2. FIG. 2 also shows that the body K of the syringe has been emptied of its content, the liquid having been injected into the body of a patient by the user. The plunger P is at the end of its stroke.

Because the catches 6 have been retracted, and when the thumb of the user ceases to exert pressure on the external end PE of the plunger, the spring R relaxes, urging the empty syringe upwards (as shown in the figures) so as to cause the flange CL of the body to snap-fasten between the edge of the orifice 9 in the cap and the catches 10, as shown in FIG. 3. The cap 8 also moves under drive of the return force of the spring R towards the position shown in FIG. 3 in which the rings 7 and 11 co-operate with each other to limit the stroke of the cap 8 and thus the withdrawal stroke of the syringe. In the configuration shown in FIG. 3, the needle A is retracted into the tube 1, thus providing 100% safety.

FIGS. 4 to 7 show a safety assembly E constituting a second embodiment of the invention. In these figures, elements that are analogous to those of the preceding Figures are designated by references that are identical.

In this case, the tube 1 does not have the second internal housing of the first embodiment. Furthermore, the external retention means of the tube 1 are constituted by two diametrically opposite fins or lugs 15 extending substantially transversely to the axis of the tube and extended in the longitudinal direction (parallel to the axis of the tube 1) by two tabs 16 themselves terminated by oppositely-directed catches 17, 18. The lugs 15 are preferably integrally molded with the tube 1.

Two pivots 19 projecting from the outside surface of the proximal end of the tube 1 are also integrally molded with the tube 1 at 90° from the two retention lugs 15. The pivots 19 define an axis extending substantially transversely relative to the tube 1.

The two pivots 19 carry two respective identical arms 20 and 21 in the form of very widely-open U-shapes. These arms 20 and 21 are inverted by their positioning at 180°. Each arm 20, 21 has a pivot hole 22 for engaging on the corresponding pivot 19. Each arm 20, 21 has a short portion and a long portion on opposite sides of the corresponding pivot 22. The short portion is terminated by an end that is bent substantially through a right angle, carrying a catch 23. The long portion is likewise terminated by an end bent substantially through a right angle, including an internal projection 24 (see FIGS. 5 and 6).

Figure 4:
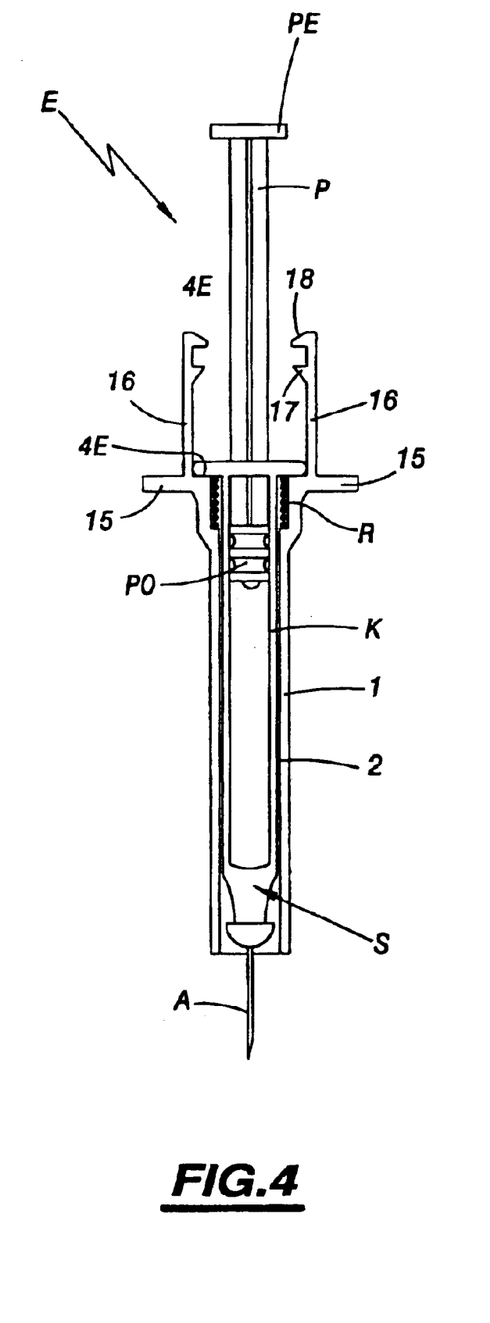
FIGS. 4 and 5 are views of a safety assembly for a syringe and constituting a second embodiment of the invention, shown in axial section on two mutually perpendicular planes, the plunger of the syringe being in its ready position.
Figure 5:
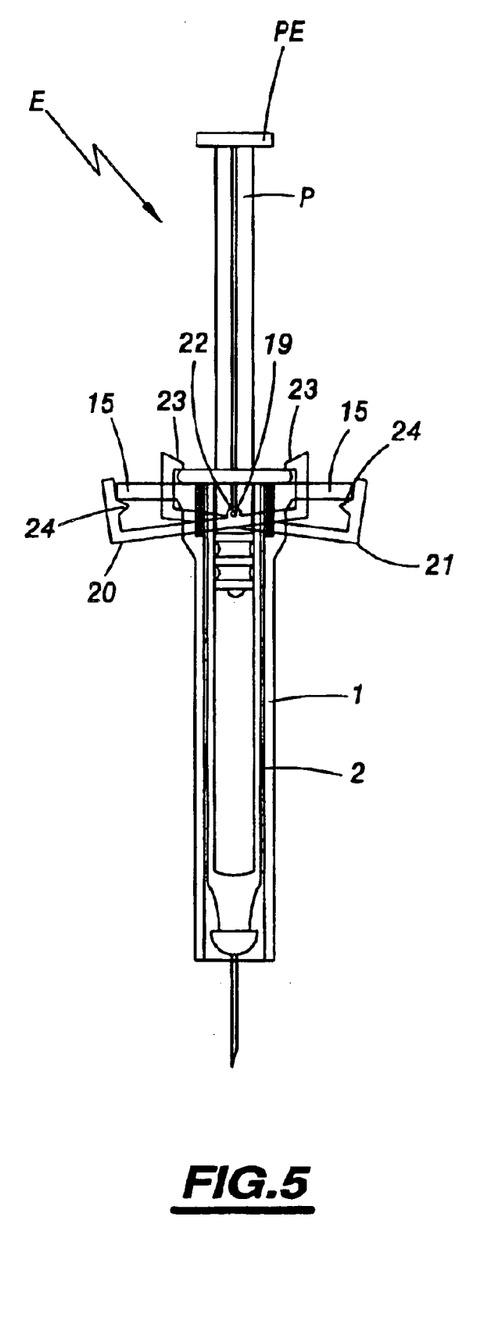

Both arms 20 and 21 are hinged about a common axis, and together they form a retractable clamp for holding the flange CL of the body of the syringe pressed against the seat 4E defined by the edge of the proximal end of the tube 1.

The bent ends of the short and long portions of the arms 20 and 21 respectively form ends for clamping the flange CL against the seat 4E and ends for driving the arms 20 and 21.

When the syringe is put into place inside the tube 1, the catches 23 retain the flange CL of the syringe in the tube 1 while compressing the spring R in the housing 3.

The arms 20 and 21 are placed in a position in which they apply forced clamping on the flange CL because their projections 24 are positioned beneath the retention lugs 15. This position is symmetrical because of the way the arms 20 and 21 are placed at 180° relative to each other (see FIG. 5).

To inject liquid into the body of a patient, the user applies two fingers (generally the index and the middle finger) simultaneously against the lugs 15 and the arms 20, 21.

Figure 6:
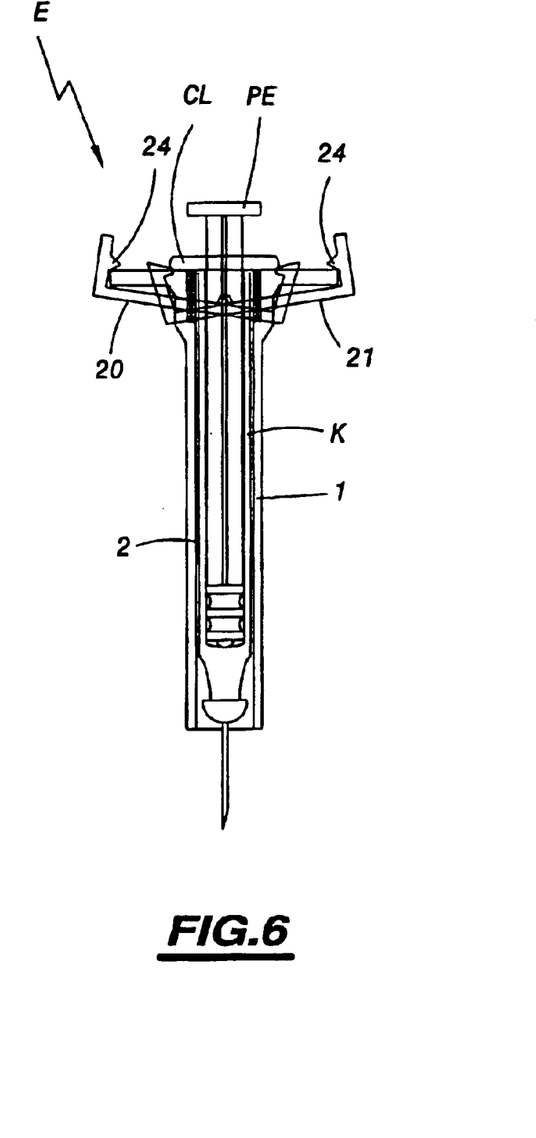
FIG. 6 is a view similar to FIG. 5 in which the plunger of the syringe in its end-of-injection position.

During injection, the drive ends of the arms 20 and 21 co-operate with the lugs 15 so as to be moved when the plunger reaches its end-of-injection position from the position in which they apply forced clamping on the flange CL as shown in FIG. 5 to a position in which they are forced to release said flange CL, as shown in FIG. 6. The passage from the forced clamping position to the forced release position of the flange takes place by passing through a hard point and by elastic deformation of the arms 20 and 21. At the end of injection, the user presses hard against the outside end CE of the plunger so as to expel all of the liquid contained in the syringe. This action causes the projections 24 to escape from the lugs 15, thereby moving the lugs 23 away from the flange CL and releasing the spring R.

Figure 7:
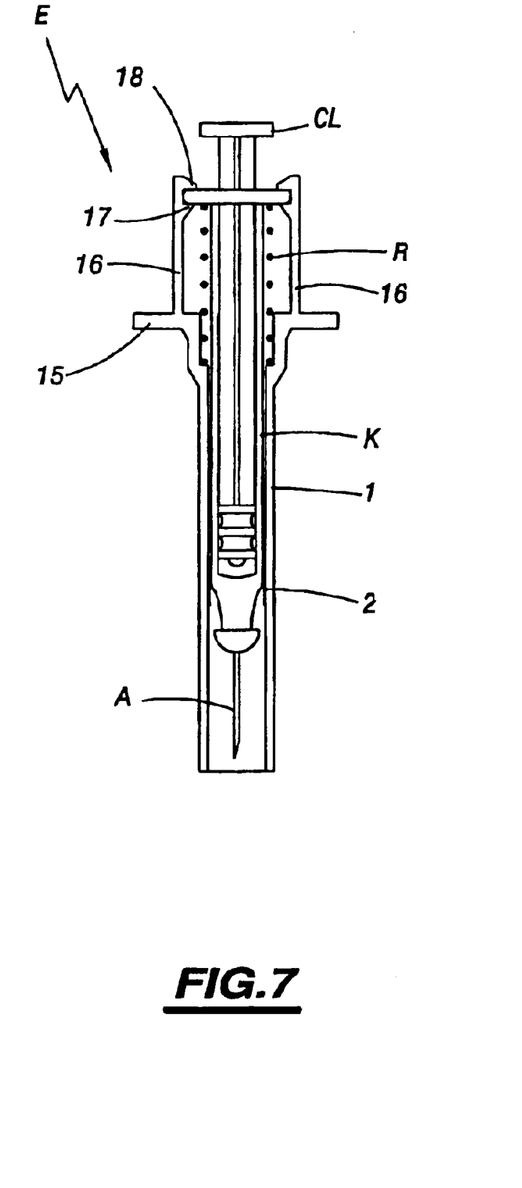
FIG. 7 is a view similar to FIG. 4 showing the position of the plunger of the syringe after the means for locking the body of the syringe has been released.

By relaxing, the spring R pushes the syringe between the tabs 16. The flange CL on the body of the syringe then co-operates with the two tabs 16 that extend the proximal end of the tube 1 by snap-fastening therewith. The locking of the flange CL between the catches 17 and 18 limits the stroke K of the syringe after the spring R has relaxed, as can be seen in FIG. 7. In FIG. 7, the needle of the syringe is retracted inside the tube 1 after being automatically withdrawn so as to be protected inside the tube 1 from any possible contact.

It should be observed that syringes prefilled with vaccine must be conserved and transported at low temperature. For practical and economic reasons, it is desirable to reduce as much as possible the overall dimensions of the needle protection means, since any increase in the volume of these protection means has repercussions on the storage and transport of injection assemblies. In addition, the injection of certain vaccines is preceded by a "vein" test which consists in jabbing the needle into the body of a patient, holding the syringe firmly, and pulling on the outside end of the plunger so as to establish suction. If a small trace of blood appears in the portion of the syringe where the needle is fixed, then injection must not be performed. The user must then jab the patient again a few centimeters away from the preceding jab. Under no circumstances must the vaccine be injected into the blood circulation network.

FIGS. 8 to 13 show a safety assembly E constituting a third embodiment of the invention. This embodiment makes it possible in particular to use a syringe that contains a vaccine.

In FIGS. 8 to 13, elements that are analogous to those of the preceding figures, are designated by references that are identical.

Figure 8:
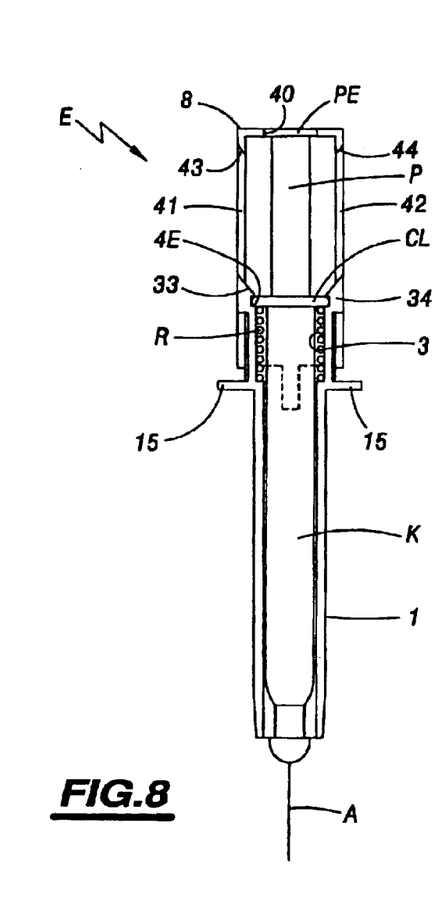
FIGS. 8 to 10 are axial section views of a safety assembly for a syringe and constituting a third embodiment of the invention, shown in three configurations of use, respectively.
Figure 9:
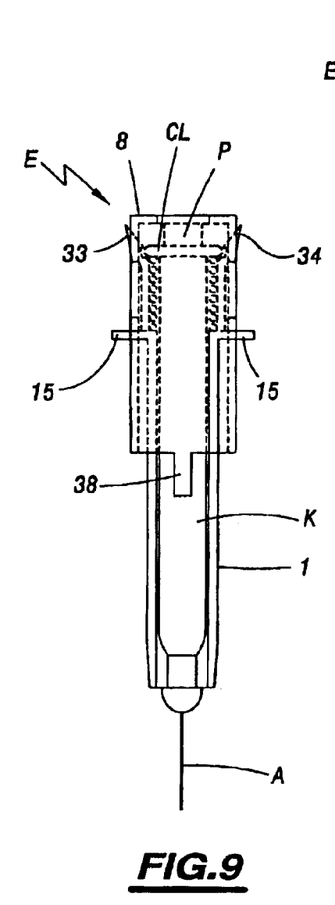
Figure 10:
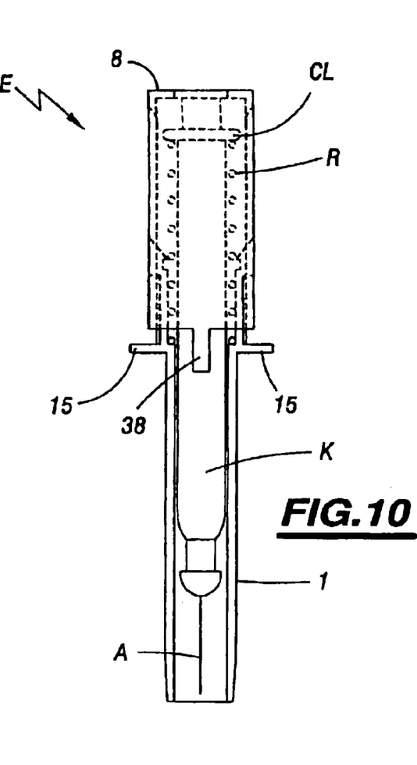

In FIGS. 8 to 10, there can be seen elements that are analogous to the elements of the preceding embodiments, namely a tube 1 containing the housing 3 in which the spring R is located. The proximal end of the tube 1 is extended by two catches 33 and 34 which are preferably diametrically opposite. In a variant, the number of catches 33, 34 could be less than or greater than two. The catches 33, 34 constitute locking means having the function of preventing the body K of the syringe from moving relative to the tube by clamping the flange CL of said body between the catches 33, 34 and the bearing seat 4E. The function of the catches 33, 34 is thus analogous to the function of the catches 6 in the first embodiment of the invention.

Two retention fins 35, 36 analogous to the lugs 15 of the second embodiment are integrally mole de with the proximal end of the tube 1 and are disposed at 180° to each other. The tube 1 is shown from the assembly E in FIG. 11. The cap 8 (see in particular FIGS. 12 and 13) is provided in this case with two substantially diametrically opposite longitudinally-extending tongues 38 and 39 which extend its distal end. The proximal end of the cap 8 is pierced by a hole 40. The cap 8 also has complementary means for preventing relative rotation between the sheath or tube 1 and the cap 8 comprising two vertical longitudinal slots 41 and 42 that are offset by 90° from the tongues 38, 39.

Figure 12:
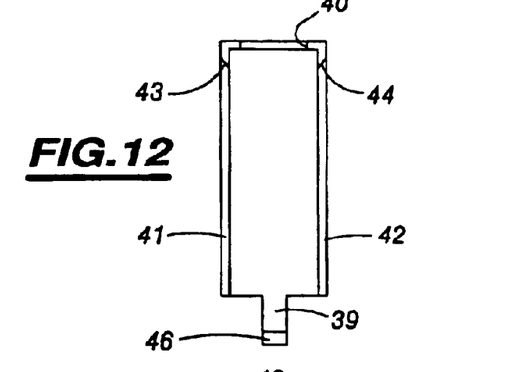
FIGS. 12 and 13 are views of the cap of the injection assembly shown in FIGS. 8 to 10, in axial section on two mutually perpendicular planes
Figure 13:
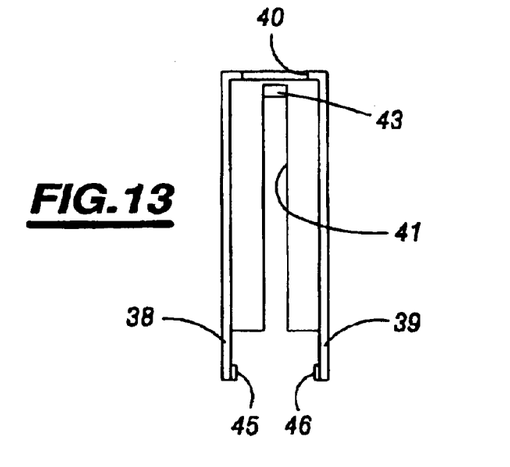

The slots 41, 42 co-operate with the fins 15 by receiving them in such a manner as to form complementary means for preventing the cap 8 from rotating relative to the tube 1.

The catches 33, 34 are retractable so as to release the flange CL by co-operating with ramps 43, 44 defining the proximal ends of the slots 41, 42.

The hole 40 in the cap serves to receive the plunger in the injection assembly. The plunger P is secured to the cap 8 by conventional means (not shown).

FIG. 8 shows the safety assembly E in a configuration ready for use, the needle of the syringe projecting through the distal end of the tube 1. Starting from this configuration, the user performs an injection, in particular an intramuscular or a subcutaneous injection, by holding the tube 1 between the index and middle fingers, and using the fins 15 while pressing the thumb against the outside end PE of the plunger. Since the cap 8 is secured to the plunger P, the cap is pushed under pressure from the thumb in the same direction as the plunger P until it reaches the position shown in FIG. 9.

When the plunger P reaches its end-of-injection position, as shown in FIG. 9, the cap 8 moves away the catches 33, 34, by means of the ramps 43, 44 of the cap 8 co-operating with the catches 33, 34, thereby releasing the spring R.

The spring then urges the empty syringe body towards the proximal end of the cap 8, as shown in FIG. 10.

After the catches 33, 34 have been released, the stroke of the cap 8 is limited by snap-fastening means opposing the resilient return force of the spring R. These snap-fastening means comprise locking studs 45, 46 formed on the free ends of the tongues 38, 39 co-operating with diametrically opposite holes 47 formed in the proximal end of the tube 1 by engaging therein (see FIG. 11).

FIG. 10 shows the configuration of the safety assembly E after use, and it can be seen that the needle is retracted inside the tube 1.

In the third embodiment of the invention, the syringe and the needle are indeed automatically-withdrawable, with the tube 1 constituting a stable portion that acts as a fixed bearing portion.

Figure 11:
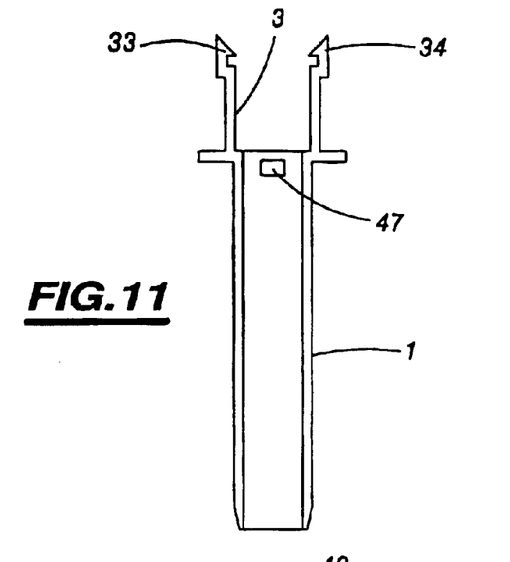
FIG. 11 is an axial section view of the protective sheath of the injection assembly shown in FIGS. 8 to 10.

It should be observed that the fins 35, 36 of the tube 1 provide stability on a non-plane surface.

The embodiments described above enable the needle to be retracted accurately in line relative to its insertion, while also performing an anti-accident function for health care personnel.

Accidental contagion becomes impossible since the distal end of the tube 1 is of small diameter, e.g. 9 millimeters (mm) thus preventing any accidental insertion of a user's finger. The safety of the assembly E is thus practically 100%, and, in accordance with the object of the invention, the safety feature is triggered (the needle is retracted) automatically and independently of human will.

Furthermore, the needle is retracted using one hand only and without requiring any special action to be taken, complying with medical regulations and also with the normal practices of health care personnel.

The invention also enables health care personnel and other people called on to handle, transport, or destroy used needles to avoid any risk of accidents.

What is claimed is:

1. A safety assembly for a prefilled syringe for injecting liquid, the syringe comprising a tubular body forming a reservoir for the liquid, carrying a needle for injecting the liquid, and having a plunger mounted in the body to be movable between a ready position and an end-of-injection position, the body of the syringe having a proximal end provided with a flange, the assembly further comprising:

a tubular sheath in which the body of the syringe is designed to be housed in axially displaceable manner between an active position in which the needle projects through a distal end of the sheath and a protection position in which the needle is retracted inside the sheath;

resilient return means for urging the body towards its protection position;

locking means for preventing the body from moving relative to the sheath in the active position by opposing the resilient force of the return means;

release means for releasing said locking means when the plunger is in its end-of-injection position;

the locking means comprising two diametrically opposite lugs formed in a wall of the tubular sheath, each lug having a free end provided with a retractable catch;

a cap mounted to slide axially on the sheath between two positions and having a proximal end with a hole for receiving the plunger;

snap-fastening means comprising an internal catch for securing the cap to the tubular body, so that due to retraction of the retractable catches, the cap is moved by resilient return means; and two complementary shoulders acting as abutments, one on the cap, the other one on the tubular sheath, to limit the stroke of the cap once the locking means have been released, in opposition to the resilient force of the return means.

2. The assembly according to claim 1, wherein the sheath carries external retention means for being held by the fingers of a user to inject the liquid by moving a drive end of the plunger axially towards the retention means.

3. The assembly according to claim 2, wherein the retention means of the sheath comprise two substantially diametrically opposite fins or lugs.

4. The assembly according to claim 2, wherein the retention means comprise a shoulder formed on the outside surface of the sheath.

5. The assembly according to claim 1, wherein the means for resiliently urging the body of the syringe into the protection position comprise a thrust spring designed to bear against an internal bearing shoulder formed in the sheath.

6. The assembly according to claim 1, wherein the sheath and the cap are generally in the form of bodies of revolution and have complementary means for preventing relative rotation between each other.

7. The assembly according to claim 6, wherein the complementary means for preventing relative rotation of the sheath and the cap comprise at least one longitudinal groove formed in the cap and co-operating with a corresponding finger secured to the sheath.

8. The assembly according to claim 6, wherein the complementary means for preventing relative rotation of the sheath and the cap comprise at least one axial slot formed in the cap and co-operating with a fin.

9. The safety assembly according to claim 1 further comprising an injection device comprising a prefilled syringe for injecting liquid, the syringe comprising a tubular body forming a reservoir for the liquid, carrying a needle for injecting the liquid, and having a plunger mounted in the body to be movable between a ready position and an end-of-injection position.

10. The safety assembly according to claim 2 further comprising an injection device comprising a prefilled syringe for injecting liquid, the syringe comprising a tubular body forming a reservoir for the liquid, carrying a needle for injecting the liquid, and having a plunger mounted in the body to be movable between a ready position and an end-of-injection position.

11. The safety assembly according to claim 3 further comprising an injection device comprising a prefilled syringe for injecting liquid, the syringe comprising a tubular body forming a reservoir for the liquid, carrying a needle for injecting the liquid, and having a plunger mounted in the body to be movable between a ready position and an end-of-injection position.

12. The safety assembly according to claim 4 further comprising an injection device comprising a prefilled syringe for injecting liquid, the syringe comprising a tubular body forming a reservoir for the liquid, carrying a needle for injecting the liquid, and having a plunger mounted in the body to be movable between a ready position and an end-of-injection position.

13. The safety assembly according to claim 5 further comprising an injection device comprising a prefilled syringe for injecting liquid, the syringe comprising a tubular body forming a reservoir for the liquid, carrying a needle for injecting the liquid, and having a plunger mounted in the body to be movable between a ready position and an end-of-injection position.

14. The safety assembly according to claim 6 further comprising an injection device comprising a prefilled syringe for injecting liquid, the syringe comprising a tubular body forming a reservoir for the liquid, carrying a needle for injecting the liquid, and having a plunger mounted in the body to be movable between a ready position and an end-of-injection position.

15. The safety assembly according to claim 7 further comprising an injection device comprising a prefilled syringe for injecting liquid, the syringe comprising a tubular body forming a reservoir for the liquid, carrying a needle for injecting the liquid, and having a plunger mounted in the body to be movable between a ready position and an end-of-injection position.

16. The safety assembly according to claim 8 further comprising an injection device comprising a prefilled syringe for injecting liquid, the syringe comprising a tubular body forming a reservoir for the liquid, carrying a needle for injecting the liquid, and having a plunger mounted in the body to be movable between a ready position and an end-of-injection position.

17. A safety assembly for a prefilled syringe for injecting liquid, the syringe comprising a tubular body forming a reservoir for the liquid, carrying a needle for injecting the liquid, and having a plunger mounted in the body to be movable between a ready position and an end-of-injection position, the body of the syringe having a proximal end provided with a flange, the assembly further comprising:

a tubular sheath in which the body of the syringe is designed to be housed in axially displaceable manner between an active position in which the needle projects through a distal end of the sheath and a protection position in which the needle is retracted inside the sheath;

resilient return means for urging the body towards its protection position;

locking means for preventing the body from moving relative to the sheath in the active position by opposing the resilient force of the return means, said locking means being released by release means when the plunger is in its end-of-injection position;

the locking means comprising two diametrically opposite lugs formed in a wall of the tubular sheath, each lug having a free end provided with a retractable catch;

a cap mounted to slide axially on the sheath between two positions and having a proximal end with a hole for receiving the plunger;

an internal catch for snap-fastening the flange of the tubular body to the cap, so that due to retraction of the retractable catches, the cap is moved by resilient return means; and two complementary shoulders acting as abutments, one on the cap, the other one on the tubular sheath, to limit the stroke of the cap once the locking means have been released, in opposition to the resilient force of the return means;

wherein the sheath and the cap are generally in the form of bodies of revolution and have complementary means for preventing relative rotation between each other; and wherein the complementary means for preventing relative rotation of the sheath and the cap comprise at least one longitudinal groove formed in the cap and co-operating with a corresponding finger secured to the sheath.

18. A safety assembly for a prefilled syringe for injecting liquid, the syringe comprising a tubular body forming a reservoir for the liquid, carrying a needle for injecting the liquid, and having a plunger mounted in the body to be movable between a ready position and an end-of-injection position, the body of the syringe having a proximal end provided with a flange, the assembly further comprising:

a tubular sheath in which the body of the syringe is designed to be housed in axially displaceable manner between an active position in which the needle projects through a distal end of the sheath and a protection position in which the needle is retracted inside the sheath;

resilient return means for urging the body towards its protection position;

locking means for preventing the body from moving relative to the sheath in the active position by opposing the resilient force of the return means, said locking means being released by release means when the plunger is in its end-of-injection position;

the locking means comprising two diametrically opposite lugs formed in a wall of the tubular sheath, each lug having a free end provided with a retractable catch;

a cap mounted to slide axially on the sheath between two positions and having a proximal end with a hole for receiving the plunger;

an internal catch for snap-fastening the flange of the tubular body to the cap, so that due to retraction of the retractable catches, the cap is moved by resilient return means; and two complementary shoulders acting as abutments, one on the cap, the other one on the tubular sheath, to limit the stroke of the cap once the locking means have been released, in opposition to the resilient force of the return means;

wherein the sheath and the cap are generally in the form of bodies of revolution and have complementary means for preventing relative rotation between each other; and wherein the complementary means for preventing relative rotation of the sheath and the cap comprise at least one axial slot formed in the cap and co-operating with a fin.

19. The safety assembly according to claim 17 further comprising an injection device comprising a prefilled syringe for injecting liquid, the syringe comprising a tubular body forming a reservoir for the liquid, carrying a needle for injecting the liquid, and having a plunger mounted in the body to be movable between a ready position and an end-of-injection position.

20. The safety assembly according to claim 18 further comprising an injection device comprising a prefilled syringe for injecting liquid, the syringe comprising a tubular body forming a reservoir for the liquid, carrying a needle for injecting the liquid, and having a plunger mounted in the body to be movable between a ready position and an end-of-injection position.

21. An assembly according to claim 1, wherein the release means comprises a ramp on the cap.

* * * * *

UNITED STATES PATENT AND TRADEMARK OFFICE
CERTIFICATE OF CORRECTION

PATENT NO. : 6,872,190 B1
DATED : March 29, 2005
INVENTOR(S) : Roger Denis et al.

It is certified that error appears in the above-identified patent and that said Letters Patent is hereby corrected as shown below:

<u>Column 4,</u>
Line 44, please delete the word "comprising" and add -- for preventing the syringe body from moving relative to the sheath or tube 1. The locking means comprise --.

Signed and Sealed this

Twelfth Day of July, 2005

JON W. DUDAS
*Director of the United States Patent and Trademark Office*

UNITED STATES PATENT AND TRADEMARK OFFICE
CERTIFICATE OF CORRECTION

PATENT NO. : 6,872,190 B1
DATED : March 29, 2005
INVENTOR(S) : Denis et al.

It is certified that error appears in the above-identified patent and that said Letters Patent is hereby corrected as shown below:

<u>Column 4,</u>
Lines 19-26, delete "The body K is held stationary relative to the tube 1 by locking means for preventing the syringe body from moving relative to the sheath or tube 1. The locking means comprise firstly a seat 4E against which the flange CL bears, the seat being formed by the internal shoulder defining the second housing 4, and secondly retractable means for clamping flange CL against the seat 4E and carried by the proximal end of the tube 1." and insert -- The body K is axially displaceable inside the tube 1 between an active position in which the needle A projects through a distal (bottom) end of the tube 1, and a protection position in which the needle A is retracted inside the tube 1. The active position is shown in Figures 1 and 2. The protection position is shown in Figure 3. --.

Signed and Sealed this

Twenty-first Day of March, 2006

JON W. DUDAS
*Director of the United States Patent and Trademark Office*